United States Patent
Nilsson

[11] Patent Number: 6,138,678
[45] Date of Patent: Oct. 31, 2000

[54] MALE INCONTINENCE GUARD

[76] Inventor: Leif Nilsson, Blabarsvagen 1, S-260 40, Viken, Sweden

[21] Appl. No.: 09/269,913
[22] PCT Filed: Sep. 30, 1997
[86] PCT No.: PCT/SE97/01641
§ 371 Date: Mar. 31, 1999
§ 102(e) Date: Mar. 31, 1999
[87] PCT Pub. No.: WO98/14146
PCT Pub. Date: Apr. 9, 1998

[30]  Foreign Application Priority Data

Oct. 3, 1996 [SE] Sweden ................... 9603611

[51] Int. Cl.$^7$ ...................................... A61F 5/48
[52] U.S. Cl. ............... 128/885; 128/DIG. 25; 600/29
[58] Field of Search ................. 128/885, 886, 128/DIG. 25; 600/29–31

[56] References Cited

U.S. PATENT DOCUMENTS

| | | | |
|---|---|---|---|
| 678,943 | 7/1901 | Davis | 128/885 |
| 2,533,924 | 12/1950 | Foley . | |
| 2,756,753 | 11/1956 | Means | 128/885 |
| 3,155,096 | 11/1964 | Outwin | 128/885 |
| 3,636,948 | 1/1972 | Atchley | 600/41 |
| 3,866,611 | 2/1975 | Baumrucker . | |
| 4,800,900 | 1/1989 | French . | |
| 4,880,016 | 11/1989 | Worth et al. . | |

FOREIGN PATENT DOCUMENTS

465531 B1  5/1993  European Pat. Off. .

*Primary Examiner*—Michael A. Brown
*Attorney, Agent, or Firm*—Cowan, Liebowitz & Latman, P.C.

[57] ABSTRACT

The incontinence control device of the present invention as described includes a cloth strap adapted to encircle a penis, the strap having cooperative pressure adherence layers on portions of the inner and outer surfaces so that the strap can form a circumference when the inner adherence layer is engaged with the outer adherence layer of the strap. The inner surface of the strap also has a compressible pad adjacent the pressure adherence layer and another compressible pad in fixed relation to the first pad. An inflatable sac is affixed to the strap between the two compressible pads. A tube passes through the strap to communicate with the interior of the inflatable sac at one end of the tube. A check valve is attached at the other end of the tube. A syringe is adapted to engage the check valve so that air in the syringe can be injected through the tube into the sac to inflate the sac. In the inflated condition, the sac and incontinence control device are adapted to impinge the urethra within the penis to, thereby, restrict the flow of urine through the urethra. The sac has a predetermined free shape with a height greater than the thickness of the two compressible pads so that the sac will maintain contact with the penis even when the sac is not inflated to ensure that the strap will not slip.

17 Claims, 4 Drawing Sheets

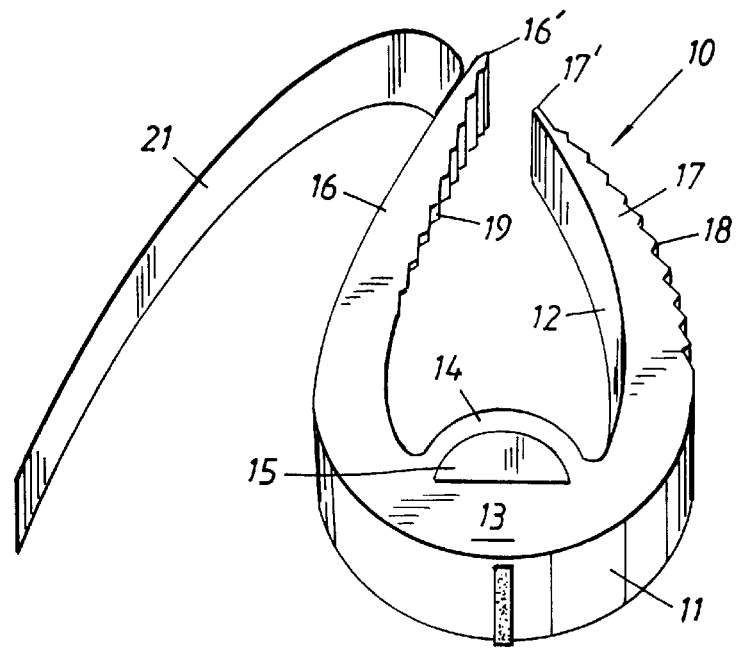
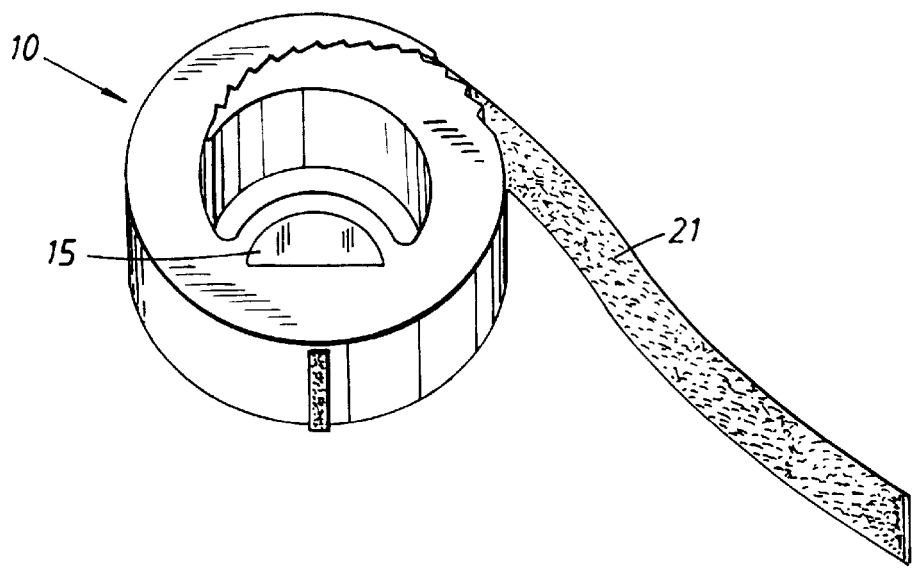

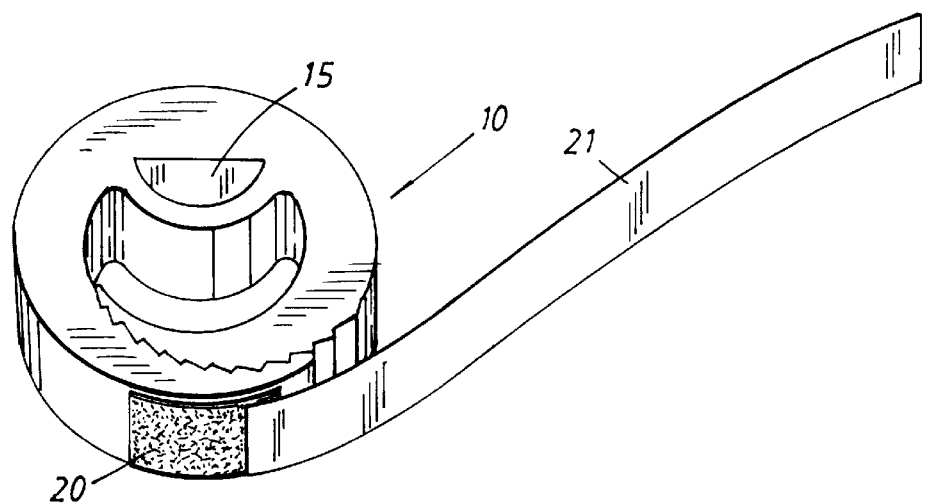
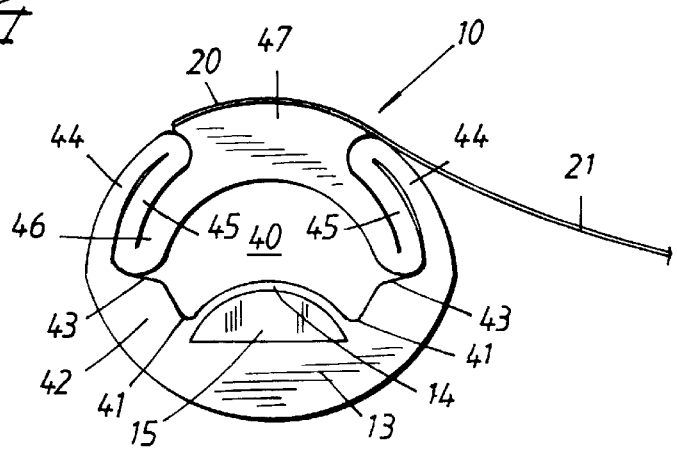

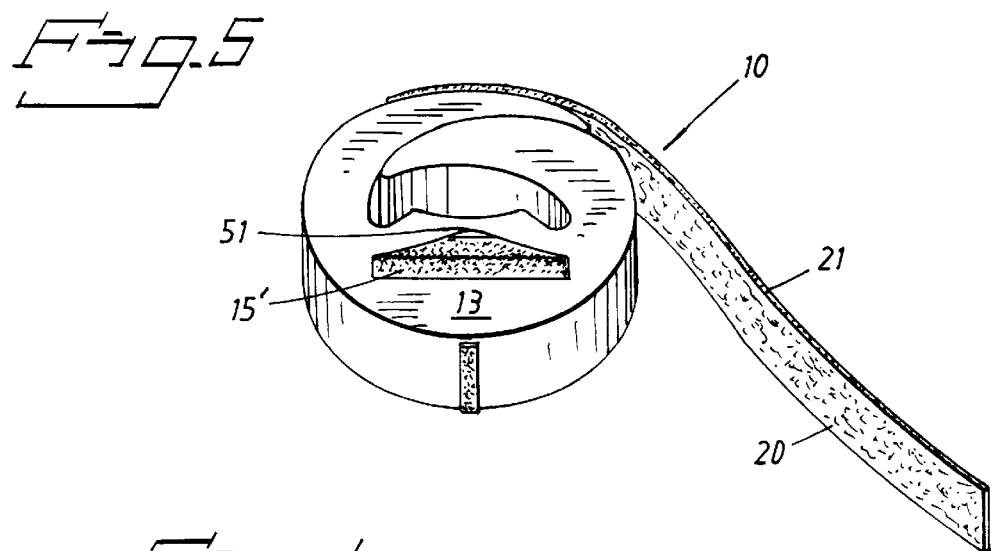
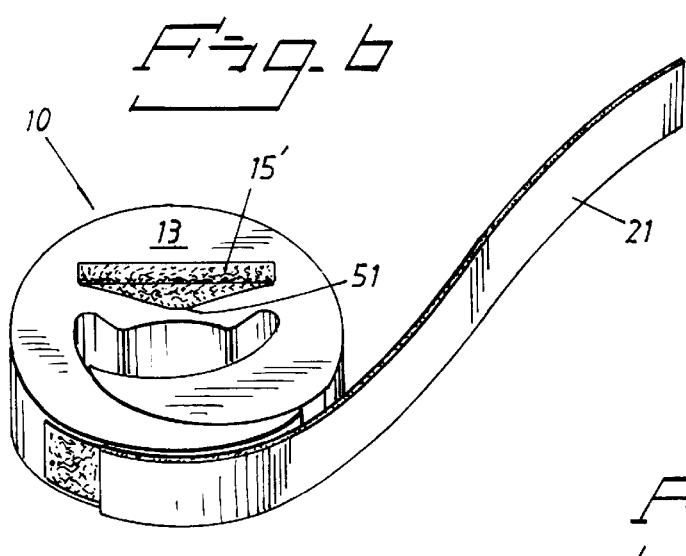
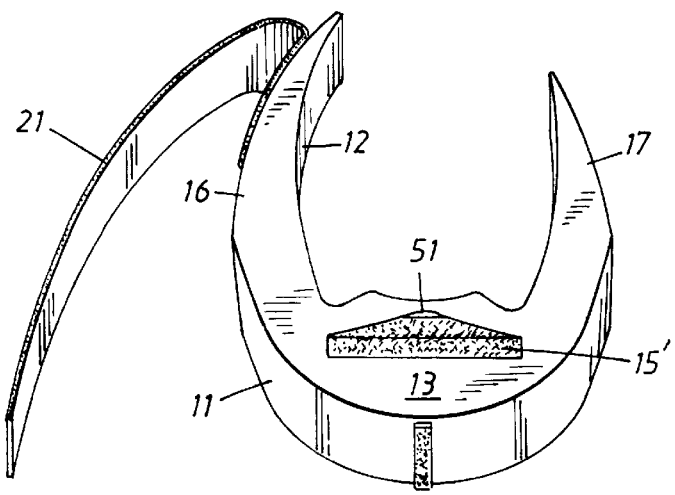

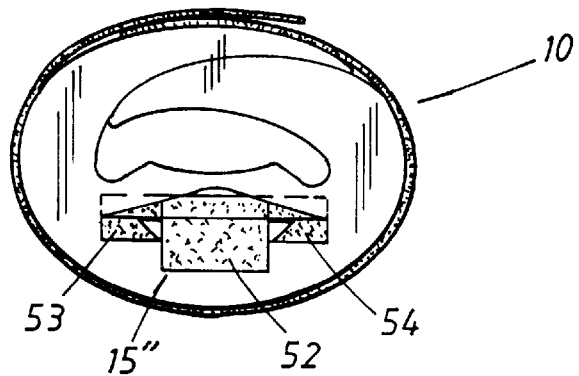
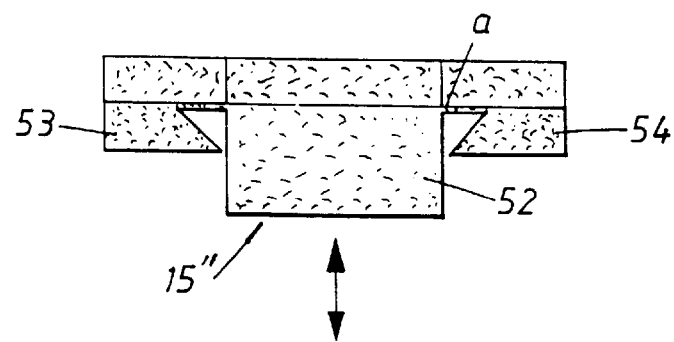

MALE INCONTINENCE GUARD

The present invention relates to a male incontinence guard of the kind that surrounds the wearer's penis, that is comprised of a relatively soft and generally elastic material, and that has a specific width and the outer surface of which coacts with a tape by means of which the incontinence guard can be affixed to the wearer's penis, wherein the inner surface of the guard that lies proximal to the penis in use includes at least one pressure element which functions to apply pressure to the corpus spongiosum penis when the tape is tightened to secure the guard around the penis, and therewith hold the penile urethra closed.

Incontinence quard users are generally males of different ages that suffer mild incontinence and elderly males and/or physically/mentally handicapped males that suffer heavier incontinence. Particularly with respect to the first group of males, i.e. those who are still physically and socially active, incontinence is a sensitive complaint which is preferably not talked about but which causes serious insecurity, particularly in gatherings of a social nature. Studies have shown that this group of males are very reluctant to discuss their problem with their doctor. A diaper is a common solution to this problem. However, diapers become ill-smelling and infected in use and cannot be worn discretely by the male user.

Also known to the art is an auxiliary aid which surrounds the wearer's penis and functions to compress the penile urethra. U.S. Pat. No. 4,800,900 teaches a device that includes generally the features set forth in the preamble of Claim 1. The means by which the penile urethra is closed has the form of an inflatable bag. This known device also includes a tape of given width and length that is placed around the penis and fixed in position with the aid of a Velcro-type fastener which joins both end parts of the device together. The device taught by this publication includes a "bag" which is connectable to a pipe or hose whose orifice contains a valve means and can be connected to an air source. Pressure is exerted against the penile urethra, when the "bag" is inflated. When the wearer wishes to urinate, he must first actuate the valve so as to release the pressure.

This known device is very complicated and is also expensive to produce. Furthermore, activation of the device requires the presence of an air source.

U.S. Pat. No. 3,866,611 teaches another type of penis clamp. This device functions in a manner similar to the aforesaid, i.e. squeezes together the penile urethra and therewith prevent an intentional urine discharge. One of the drawbacks with this known device is that it apparently causes the wearer particular discomfort. Another drawback is that it includes several pressure surfaces that are intended to compress the penile urethra at several different locations.

EP-A-0 465 530 teaches another device that has a similar function. This device is both complicated and expensive in manufacture. Neither can this device be worn. in a discrete manner that will save the wearer from embarrassment.

One object of the present invention is to provide an incontinence guard that is a functional improvement on those guards hitherto known.

Another object of the invention is to simplify the manufacture of such incontinence guards, and to provide an inexpensive but reliable product.

An incontinence guard that fulfils these objects is defined in the characterizing clause of claim 1.

So that the invention will be more readily understood and further embodiments thereof made apparent, the invention will now be described with reference to exemplifying embodiments thereof and also with reference to the accompanying drawings, in which FIG. 1 is a perspective view of a first embodiment of an inventive incontinence guard and shows the guard in a state ready to be placed around the penis of an incontinent;

FIGS. 2 and 3 are respective perspective views of the incontinence guard shown in FIG. 1, and show the guard in a use state;

FIG. 4 is a side view of a second embodiment of the improved incontinence guard;

FIGS. 5–7 illustrate a further embodiment of the invention;

FIG. 8 illustrates a further variant of the invention; and

FIG. 9 is an enlarged view of the pressure element shown in FIG. 8.

FIGS. 1–3 and 5–7 illustrate a male incontinence guard designated by the general reference 10. The incontinence guard is produced as a one-piece structure from a soft material, preferably an air-permeable plastic material, such as polypropylene, for instance. The incontinence guard 10 has an outer surface 11 and an inner surface 12. It also has a central, first thickened part 13, and the inner surface 12 has a generally semi-circular shape in the region of said first thickened part 13. This semi-circular part is referenced 14 and encloses an opening which coincides shape-wise with said semi-circular part and which is adapted to receive a pressure element 15, preferably removably, which is harder than, or much harder than the soft material from which the incontinence guard is made. This pressure element 15 may be plastically deformable or elastically supple. The pressure element 15 is surrounded top and bottom by walls. The first thickened part 13 merges at opposite ends with mutually opposing arms 16 and 17, each of which narrows towards a respective free end 16' and 17'. It will be seen that the outer surface of the arm 17 is roughened along part of its length, e.g. with serrations or ridges as indicated at 18, and the inner surface of the opposite arm 16 has corresponding roughenings 19 along a corresponding length. It will be evident from FIGS. 2 and 3 that these roughened surfaces 18 and 19 mutually coact when the incontinence guard is in use, so that when the arms 16, 17 are folded so as to overlap one another in the manner illustrated, such as to fold the guard around the penis (not shown), the surfaces will generate a frictional effect. At least one of the arms 16, 17 includes in the proximity of one end a fastener element 20 for coaction with one end of a tape 21, which when the guard 10 is in use locks against the fastener element 20 subsequent to placing the novel incontinence guard around the penis and tightening said guard. The fastener element 20 and the tape 21 may conveniently be of the touch and close fastener type.

It is assumed in FIGS. 2 and 3 that the incontinence guard has been placed around the wearer's penis. The convex part 14 of the FIG. 1 illustration thus lies against the underside of the penis. When the tape 21 is tightened, the generally rigid pressure element 15 will exert pressure on the penile urethra via the relatively thin wall-part 14 of the guard, and therewith squeeze the, urethra together and prevent the unintentional discharge of urine. The tape 21 can be loosened when the wearer wishes to urinate, therewith relieving the pressure on the urethra.

FIG. 4 shows another embodiment of the inventive male incontinence guard.

Those elements in the FIG. 4 embodiment that find correspondence in the embodiment illustrated in FIGS. 1–3 have been identified with the same reference signs. The incontinence guard 10 of this embodiment is also a one-piece structure, although in this case the guard has formed therein a through-penetrating opening 40 through which a penis (not shown) can be inserted. The guard may have a material width of about 20 mm, which enables the incontinence guard to fit stably around the root of the penis, which is the most suitable place around which to seat the incontinence guard. When the incontinence guard is in an active state, the first thickened part 13 and the pressure element 15 function as pressure element against corpus spongiosum penis. Located on either side of the first thickened part 13 is a recessed part 41 which allows air to pass between the body of the incontinence guard and the penis inserted therein. These recessed parts merge with parts 42 whose thickness is substantially smaller than the thickness of the first thickened part 13. These parts 42 are bevelled to form shoulders 43 which function as abutment surfaces for the two wall-parts 44, 45 which, in one position, are folded so as to overlap each other. The wall-parts 44, 45 have a smaller thickness than the aforesaid carts 42 and are elastic to some extent.

A fold is formed mechanically between respective wall-parts 44, 45, when manufacturing the incontinence guard. Respective parts 46, which are slightly thicker than the wall-parts 44, 45 form a continuation of respective wall-parts 45 and merge with a second thickened part 47 which lies opposite the first thickened part 13 in aporoximately the same vertical plane.

One important advantage afforded by the FIG. 4 embodiment is that the size of the opening 40 can be varied with the aid of down-folded or in-foldable parts that extend on both sides of the mutually opposing first and second thickened parts 13 and 47.

It will be obvious to the skilled person that bellows-like side walls would also fulfil the function of enabling the size of the opening 40 to be varied.

The breadth of the pressure element 15 in the vertical direction can be greater or smaller than that shown in the Figures in the case of both embodiments, although the upper part of said element 15 will preferably have an arcuate shape so as to conform with the arcuate shape of the first thickening 13. Although the upper arcuate surface of the pressure element 15 may abut the underside of the penis directly, it is preferred to permit the soft material in the incontinence guard to form a penis abutment surface of any desired thickness. Consequently, the pressure element 15 is at least partially "baked-in" in the softer material of the incontinence guard. The combination of the soft, or relatively soft, material from which the incontinence guard is made and the pressure element 15 will not cause discomfort to the wearer and will optimally prevent the involuntary discharge of urine at the same time. With regard to the illustrated embodiments, it can be said generally that the inventive incontinence guard shall have a part which lies directly or indirectly against the underside of the penis and which is of sufficient hardness to squeeze together the penile urethra when the incontinence guard is positioned correctly, therewith preventing the involuntary discharge of urine.

The embodiments illustrated in FIGS. 5, 6 and 7 of the drawings will now be described in more detail. The main difference between the incontinence guard illustrated in FIGS. 1–3 and the incontinence guard illustrated in FIGS. 5–7 consists mainly in the different configurations of the pressure element 15 and the space in which the pressure element is accommodated. The following description is therefore concentrated on these differences.

The pressure element of the inventive incontinence guard shown in FIGS. 5–7 is referenced 15' and the space which accommodates the pressure element and which has essentially the same shape as said element has been referenced 50 for the sake of illustration. The pressure element 15' has a flat, horizontal bottom surface whose length is the same as, or substantially the same as, the length extension of the space 50. The pressure element 15' has on that side which lies opposite to the bottom surface a central raised surface or bead 51 of given lateral width and extending along the full length of the pressure element 15', such as to pass beneath and parallel with a penis (not shown) inserted into the guard and, consequently, also parallel with the penile urethra. The upper defining wall of the space 50, primarily the bottom surface of said wall that faces towards the pressure element 15', has a shape which is the same or essentially the same as the shape of the upper part of the pressure element 15'. This upper surface of the defining wall has a central cupped portion in which the wearer's penis is placed. The penis, and therewith the penile urethra, is herewith guided in parallel with the incontinence guard. When a guard of the aforedescribed kind is used and the tape 21 is duly tightened, the penis will be fixed in position essentially immediately above the upstanding bead 51 on the pressure element 15' and, when the tape 21 is further tightened, will function to exert against the penile urethra a pressure which squeezes the urethra together over a given distance therealong (the longitudinal extension of the bead 51), therewith preventing the unintentional discharge of urine. The wearer is able to urinate in a normal way, by loosening the tape 21 on the incontinence guard 10.

FIG. 8 illustrates a further embodiment of the pressure element 15 and the space that accommodates said pressure element. In the FIG. 8 embodiment, the elongated pressure element, referenced 15" in this Figure, includes a flat upper surface and its underside includes a central part 52 whose bottom portion projects out downwardly. The central part 52 merges with mutually opposing side-parts 53, 54. The three-part pressure element is accommodated in the illustrated space, similar to the pressure element of the embodiments shown in FIGS. 1–3 and 4, 5–7 respectively. The upper defining wall of said space, and then its upper surface, is cupped to accommodate the curvature or the penis, and thus serves as a penis guide.

The division of the pressure element 15" into parts 52, 53, 54 is such that the central part 52 connects with respective side-parts 53, 54 at some point, either at the top or at the bottom, suitably in the form of a strap of predetermined length. This is illustrated in the drawings by the upper points a and the bottom points b.

The purpose of this arrangement is to provide an effect whereby essentially only the central part of the pressure element 15" can be moved vertically up and down (in the plane of the drawing) relative to the side-parts 53, 54. This effect can thus be obtained by hinging the central part 52 to respective side-parts 53, 54. This hinge connection between respective parts of the pressure element 15" can be used when the inventive incontinence guard is used in the following way: when the incontinence guard 10 is placed in position on the penis with the penis lying in the cupped hollow in the upper defining wall, and the tape 21 is tightened, the pressure exerted on the downwardly projecting portion of the part 52 will guide the outwardly projecting portion upwards towards the penis, and because the central part of the pressure element 15" lies parallel with the penis, the central part 52 will be pressed indirectly against the underside of the penis and therewith squeeze together the penile urethra. Depending on the length of the outwardly projecting part of the pressure element 15", a relatively heavy pressure can be applied indirectly to the penile urethra. Practical tests have shown that even severe forms of urine incontinence can be effectively controlled with such an incontinence guard.

All of the described embodiments of the inventive incontinence guard include a pressure element that is intended to lie parallel with the wearer's penis, so as to squeeze the penile urethra together alone a given part of its length. It will be understood, however, that the ridges or outwardly projecting parts of the pressure element, when such parts are included, may extend perpendicularly to the position that the penis is intended to take when the inventive guard is worn.

The pressure element of the embodiments illustrated in FIGS. 5–7 is made of cellular plastic or some corresponding material, although it may alternatively be made from any material suitable for its purpose.

FIG. 9 is a schematic illustration of the pressure element 15" of the FIG. 8 embodiment.

As with the pressure elements of the earlier described embodiments of the invention, the dimensions of the pressure element 15" of FIGS. 8, 9 are adapted to the width of the incontinence guard, i.e. the pressure element extends transversely across the guard in the space that accommodates said pressure element, at least substantially throughout the full width and length of said space. The extent to which the pressure element extends vertically (in the plane of the drawing) will vary in accordance with the extent to which the tape 21 is tightened in order to apply desired pressure to the penis (penile urethra).

The central part 52 of the pressure element 15" is connected to respective side-parts 53, 54 by means of a strap 56 //no 56 in the Figures// whose length will preferably be at least the same as the length of the outwardly protecting portion of the central part 52, typically about 5 mm. In this way, the afore-described movement of the central part 52 in relation to the side-parts 53, 54 as the tape 21 is tightened will occur over a distance that corresponds to the length of respective straps 56. When the tape 21 is loosened, so that the wearer is able to urinate, the central part 52 will return to the state shown in the Figure.

It will be understood that the invention is not restricted to the illustrated and described embodiments thereof and that modifications and variations can be made within the scope of the following Claims.

What is claimed is:

1. A male incontinence guard that includes an outer surface and an inner surface which embraces the penis of a wearer, and fastener means whereby the incontinence guard can be removably secured to the penis under pressure, wherein the inner surface includes at least one pressure element which functions to exert pressure on the corpus spongiosum penis when the guard is in use, wherein the incontinence guard is a one-piece structure made of a soft, pliable materials and includes a central part having a first thickened portion which includes an opening or cavity, and arms that extend in mutually opposite directions from the central portion; and in that said cavity or opening is adapted to accommodate a pressure element that has a degree of hardness such as to exert pressure on the penile urethra and therewith prevent unintentional discharge of urine when the incontinence guard is worn and in its active state.

2. An incontinence guard according to claim 1, wherein the opening or cavity has a semi-circular shape with the convex part orientated on the inner surface of the guard and functioning to exert a generally punctiform pressure against the underside of the penis.

3. An incontinence guard according to claim 1, characterized in that the pressure element is elastically deformable.

4. An incontinence guard according to claim 1, characterized in that the pressure element is elastically deformable.

5. An incontinence guard according to any one of claims 1–4 having adhesive for affixing the pressure element in said opening or cavity.

6. An incontinence guard according to claim 1, characterized in that the pressure element is non-deformable.

7. An incontinence guard according to claim 1, characterized in that the thickness of the arms decreases towards respective end parts of said arms; and in that the outer surface of one arm and the inner surface of the other arm include friction enhancing means in at least the end regions of respective arms.

8. An incontinence guard according to claim 7, characterized in that the folded side-wall parts on respective opposite sides of the pressure element are at least two in number.

9. An incontinence guard according to claim 1, characterized in that the side-walls located on respective opposite sides of the pressure element are folded so as to overlap in an inactive initial position and therewith form extensions that can be pulled out and in when required, and in that said wall-parts preferably have a smaller, or much smaller thickness than remaining parts of the incontinence guard.

10. An incontinence guard according to claim 1, characterized in that the side-wall parts located on respective opposite sides of the pressure element have a bellows structure which enable the penis receiving opening to be enlarged when necessary.

11. An incontinence guard according to claim 10, characterized in that the upper defining wall of the pressure-element accommodating space has a cupped shape such as to form a guide for the penis of the wearer.

12. An incontinence guard according to claim 11, wherein the hinge connection between the central part and respective side-parts is comprised of a strap whose length corresponds essentially to the length of the downwardly projecting portion of said central part.

13. An incontinence guard according to claim 10, wherein the pressure element is comprised of three mutually hinged parts; in that the central part of the pressure element includes a downwardly facing projecting part in addition to said upwardly projecting bead; and in that the parts of said pressure element are so hinged together that the pressure applied to the outwardly and downwardly projecting bottom part will cause essentially only said central part to move upwards such as to cause said bead to exert a force indirectly on the wearer's penis and therewith on the penile urethra.

14. An incontinence guard according to claims 11 or 13, wherein the hinge connection is disposed at or in the region of the top or bottom end-parts.

15. An incontinence guard according to claim 10, wherein the bead on said pressure element extends transversely to the longitudinal axis of the wearer's penis.

16. An incontinence guard according claim 10 wherein the pressure element is made of a cellular plastic.

17. An incontinence guard according to any one of claim 1, characterized in that the generally upper central part of the pressure element has an upwardly projecting bead or like raised surface that extends along the full length or along substantially the full length of said pressure element parallel with the penis enclosed in said incontinence guard.

* * * * *